US00PP18254P2

(12) United States Plant Patent
Eggleton

(10) Patent No.: US PP18,254 P2
(45) Date of Patent: Nov. 27, 2007

(54) ***LAVANDULA* PLANT NAMED 'VIOLET LACE'**

(50) Latin Name: *Lavandula stoechas*
Varietal Denomination: Violet Lace

(76) Inventor: Steven Eggleton, 3 Harris Rd Wonga Park, Melbourne, Vic (AU), 3115

( * ) Notice: Subject to any disclaimer, the term of this patent is extended or adjusted under 35 U.S.C. 154(b) by 24 days.

(21) Appl. No.: 11/429,166

(22) Filed: May 4, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV ROM GTITM Computer Database Citation for 'Violet Lace' 2006/04.*

* cited by examiner

*Primary Examiner*—Wendy C Haas

(57) ABSTRACT

A new cultivar of *Lavandula* plant named 'VIOLET LACE' that is characterized by upright open habit, early blooming, fragrant green foliage, fragrant red-purple flower spikes with small greyed-purple sterile bracts. These traits set 'VIOLET LACE' apart from all other existing varieties of *Lavandula* known to the inventor.

2 Drawing Sheets

Genus: *LAVANDULA.*
Species: *stoechas.*
Denomination: 'VIOLET LACE'.

BACKGROUND OF THE INVENTION

The present invention relates to a new and distinct cultivar of lavender known botanically as *Lavandula stoechas* and hereinafter referred to by the cultivar name 'VIOLET LACE'.

The new *Lavandula* cultivar named 'VIOLET LACE' is one individual selection in the Australian lavender 'Lace Series' that resulted from a formal breeding program. The breeding program was established in November 2001 and conducted by the inventor at the inventor's nursery in Victoria, Australia. The inventor, a specialist of the genus *Lavandula,* selected 'VIOLET LACE' in September 2003. Selection was based on the criterion of strong commercial sales potential due to early flowering, hardiness, and strong landscape performance.

'VIOLET LACE' is a selection arising from the controlled cross-pollination of *Lavandula stoechas* 'Kew Red' (unpatented) as the female parent and *Lavandula stoechas* 'Pukehou' (unpatented) as the male parent. Cross-pollination of the parent plants took place in Park Orchards, Victoria, Australia. From this cross a seedling population was raised in February 2002, and grown to flowering maturity in 140 mm. containers in September 2002. From these seedlings the final selection was made.

'VIOLET LACE' is a perennial suitable for use in the landscape. Cultural requirements include full sun, adequate but not excess water, and well-draining soil. Mature height and breadth is 70 cm. 'VIOLET LACE' exhibits upright, open habit, scented green foliage, and scented red-purple flower spikes in spring and summer. Sterile bracts are small and greyed-purple in color.

The traits that distinguish 'VIOLET LACE' from all other *Lavandula* known to the inventor are early flowering, sterile bract size, plant habit, peduncle length, and sterile bract color. 'VIOLET LACE' is distinguishable from the female parent by length and color of sterile bracts. An individual sterile bract of 'VIOLET LACE' is long and mid-violet in color when compared to the sterile bract of 'Kew Red', which is short and pink. 'VIOLET LACE' is distinguishable from the male parent by medium peduncle length, dense habit and dark mid-violet sterile bracts. In comparison, 'Pukehou' has a long peduncle, medium to sparse plant density, and dark violet sterile bracts.

The new *Lavandula* cultivar named 'VIOLET LACE' was first asexually propagated by the inventor in 2003. Asexual propagation was accomplished at the inventor's nursery in Victoria, Australia using tip cuttings. Since that time 'VIOLET LACE' has been determinated stable, and reproduces true to type in successive generations of asexual propagation.

SUMMARY OF THE INVENTION

The following traits have been repeatedly observed and represent the distinguishing characteristics of the new *Lavandula* cultivar named 'VIOLET LACE'. These traits in combination distinguish 'VIOLET LACE' from all other existing varieties of *Lavandula* known to the inventor. 'VIOLET LACE' has not been tested under all possible conditions and phenotypic differences may be observed with variations in environmental, climatic, and cultural conditions, without however, any variance in genotype.

1. 'VIOLET LACE' exhibits upright, open habit.
2. 'VIOLET LACE' exhibits small scented red-purple flower spikes with greyed-purple sterile bracts.
3. 'VIOLET LACE' exhibits fragrant green foliage.
3. 'VIOLET LACE' is one selection in the Australian lavender 'Lace Series' which offers early blooming with strong landscape performance.

4. Cultural requirements for 'VIOLET LACE' are full sun, adequate but not excess water and well-draining soil.
5. 'VIOLET LACE' blooms in spring and summer.
6. 'VIOLET LACE' is 70 cm in height and 70 cm. in width at maturity.
7. 'VIOLET LACE' is asexually propagated utilizing the method of tip and stem cuttings.
8. 'VIOLET LACE' is suitable for use as an ornamental in the landscape.
9. 'VIOLET LACE' is hardy to USDA Zone 8.

BRIEF DESCRIPTION OF THE DRAWINGS

The accompanying drawings illustrate the overall appearance of the new *Lavandula* cultivar named 'VIOLET LACE' showing the colors as true as it is reasonably possible to obtain in color reproductions of this type. Color in the drawings may differ from the color values cited in the detailed botanical description, which accurately describe the actual color of the new *Lavandula,* variety named 'VIOLET LACE'. The drawings were made of 9-month-old plants greenhouse grown in 16 cm. containers.

The drawing labeled

The drawing labeled

BOTANICAL DESCRIPTION OF THE PLANT

Figure 1:
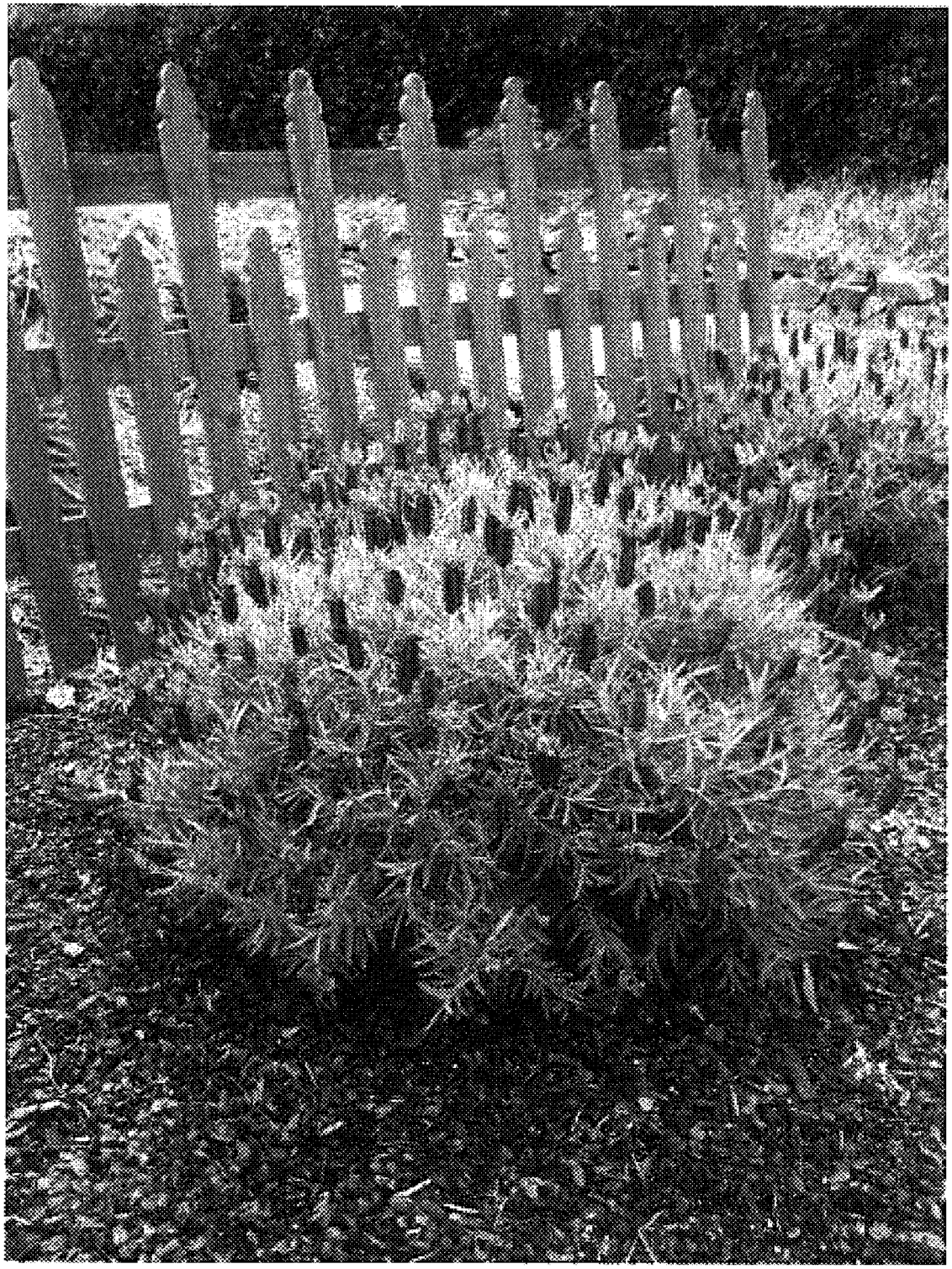
FIG. 1 depicts the plant in bloom from a side perspective.
Figure 2:
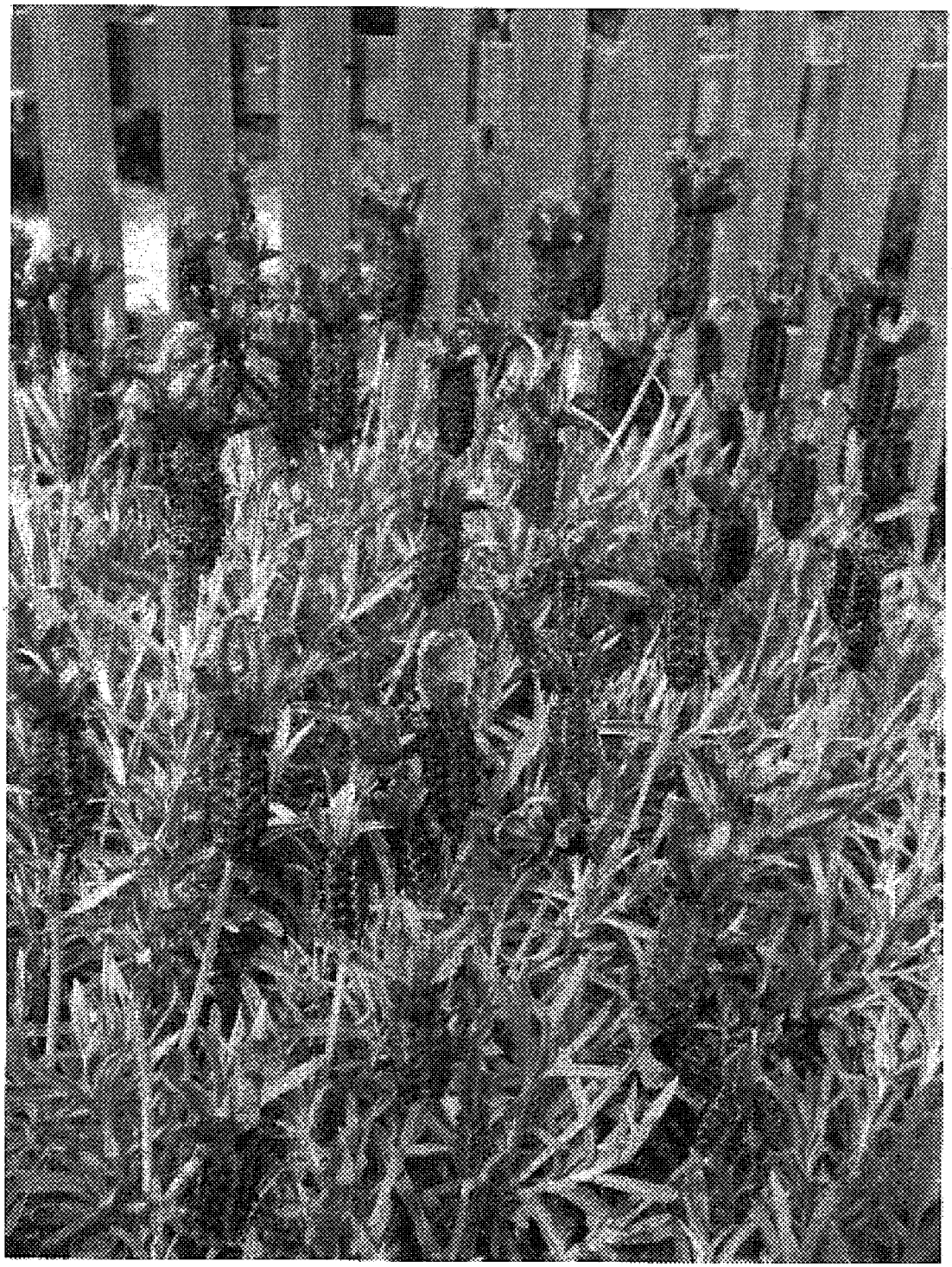
FIG. 2 depicts a close-up view of the flower spike. Drawings were made using conventional techniques and although the leaf and flower color of 'VIOLET LACE' may appear different from the actual color due to light reflectance, they are as accurate as possible by conventional photography.

The following is a detailed botanical description of the *Lavandula* cultivar named 'VIOLET LACE'. Data was collected in Arroyo Grande, Calif. from 9-month-old plants greenhouse grown in 16 cm commercial containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'VIOLET LACE'.
*Family.*—Lamiaceae.
*Genus.*—*Lavandula.*
*Species.*—*stoechas.*
*Variety denomination.*—'VIOLET LACE'.
*Common name.*—Lavender.

Plant:

*Habit.*—Upright and open.
*Height* (*at maturity*).—70 cm.
*Width* (*at maturity*).—70 cm.
*Life cycle.*—Perennial.
*Use.*—Ornamental for the landscape.
*Vigous.*—Moderate.
*Hardiness.*—USDA Zone 8.
*Propagation.*—Tip and stem cuttings.
*Root system.*—Fibrous.
*Cultural requirements.*—Full sun, adequate but not excess water, and well-draining soil.
*Time to produce a rooted cutting.*—4–6 weeks.
*Time to produce a* 10 cm container plant in bloom.—20 weeks.
*Seasonal interest.*—Flower spikes in spring and summer.
*Parentage.*—*Lavandula stoechas* 'VIOLET LACE' is a selection that resulted from controlled cross-pollination of the following parents: Female parent plant: *Lavandula stoechas* 'Kew Red'. Male parent plant: *Lavandula stoechas* 'Pukehou'.
*Disease and insect resistance or susceptibility.*—Minimal disease and insect susceptibility, with occasional aphids on new growth.

Stem:

*Branching.*—Freely branching.
*Stem shape.*—Quadrangular.
*Stem surface.*—Pubescent.
*Tomenta color.*—156D.
*Stem color.*—145B.
*Stem length.*—Average is 8 cm.
*Stem width.*—1.50 mm.
*Stem fragrance.*—Resinous scent.
*Internode length.*—Range of 1.5 cm–2.0 cm.

Foliage:

*Leaf arrangement.*—Opposite.
*Leaf division.*—Simple.
*Leaf shape.*—Linear.
*Leaf margin.*—Entire.
*Leaf apex.*—Broadly acute.
*Leaf base.*—Attenuate.
*Leaf attachment.*—Sessile.
*Leaf color* (*adaxial surface*).—138A.
*Leaf color* (*abaxial surface*).—138B.
*Leaf surface* (*abaxial surface*).—Tomentose.
*Leaf surface* (*adaxial surface*).—Pubescent.
*Tomenta color.*—156D.
*Venation* (*abaxial surface*).—Reticulate with prominent mid-vein.
*Vein color* (*adaxial surface*).—138A.
*Vein color* (*abaxial surface*).—138B.
*Leaf length.*—Average is 3.50 cm.
*Leaf width.*—Average is 0.60 cm.
*Leaf fragrance.*—Resinous scent.

Inflorescence:

*Fragrance.*—Resinous scent.
*Blooming period.*—April through August.
*Inflorescence type.*—Spike.
*Spike length.*—2.50 cm.
*Spike diameter.*—1.25 cm.
*Spike shape.*—Conical.
*Spike quantity.*—Average of 14.
*Peduncle length.*—3 cm.
*Peduncle width.*—2 mm.
*Peduncle shape.*—Quadrangular.
*Peduncle color.*—N144A.
*Peduncle surface.*—Pubescent.
*Tomenta color.*—156D. (individual flower is referred to as corolla)
*Corolla number.*—Average of 12 per individual spike.
*Corolla color.*—72A.
*Corolla shape.*—Salverform.
*Corolla depth.*—8 mm.
*Corolla diameter.*—4.50 mm.
*Corolla tube depth.*—7 mm.
*Corolla tube diameter.*—1.50 mm.
*Petals.*—Four in number.
*Petals fused or unfused.*—Basally fused.

*Petal shape.*—Reniform.
*Petal length.*—1.75 mm.
*Petal width.*—1.90 mm.
*Petal apex.*—Obtuse and emarginated petal apices individually observed on an individual corolla.
*Petal margin.*—Entire.
*Petal surface* (*adaxial and abaxial*).—Glabrous.
*Petal color* (*adaxial surface*).—72A.
*Petal color* (*abaxial surface*).—72A.
*Calyx color.*—Individual colors 145A and 70A.
*Calyx shape.*—Tubular.
*Calyx surface.*—Lanate.
*Color of hairs.*—155B.
*Calyx length.*—3 mm.
*Calyx width.*—2 mm.
*Sepals.*—Four in number.
*Sepals fused or unfused.*—¾ length fused.
*Sepal apex.*—Acute. (Fertile bract)
*Fertile bract shape.*—Deltoid.
*Fertile bract length.*—0.55 cm.
*Fertile bract width.*—0.75 cm.
*Fertile bract color* (*ventral surface*).—Individual colors N186B and 145B are present on an individual fertile bract.
*Fertile bract color* (*dorsal surface*).—Individual colors N186B and 145B are present on an individual fertile bract.
*Vein pattern.*—Reticulate.
*Vein color* (*ventral and dorsal surfaces*).—N186B.
*Fertile bract apex.*—Acute.
*Fertile bract base.*—Attenuate.
*Fertile bract surfaces* (*ventral and dorsal*).—Lanate.
*Fertile bract margin.*—Entire. (Sterile bract)
*Sterile bracts.*—Average of 4 per spike.
*Sterile bract appearance.*—Petaloid.
*Sterile bract surfaces* (*abaxial and adaxial*).—Pubesent.
*Color of hairs.*—155B.
*Sterile bract shape.*—Oblanceolate.
*Sterile bract margin.*—Entire.
*Sterile bract length.*—1.50 cm.
*Sterile bract width.*—0.60 cm.
*Sterile bract apex.*—Broadly acute.
*Sterile bract base.*—Cuneate.
*Sterile bract color* (*adaxial surface*).—Individual colors 70B, and 186B are present on an individual sterile bract.
*Sterile bract color* (*abaxial surface*).—Individual colors 70B, and 186B are present on an individual sterile bract.
*Vein pattern.*—Reticulate.
*Vein color.*—70B.

Reproductive organs:
*Stamens.*—Four in number.
*Stamen form.*—Adnate to ventral surface of corolla tube.
*Stamen color.*—155C.
*Stamen length.*—4 mm.
*Anther.*—Four.
*Anther color.*—163A.
*Pollen color.*—163C.
*Pollen quantity.*—Moderate.
*Pistil.*—One.
*Pistil length.*—3 mm.
*Pistil color.*—155B.
*Stigma height.*—Less than 0.50 mm.
*Stigma surface.*—Glossy.
*Stigma shape.*—Orbicular.
*Stigma color.*—83A.
*Ovary dimensions.*—Less than 0.50 mm.
*Ovary shape.*—Globose.
*Ovary color.*—138A.
*Ovary position.*—Superior.

Seed: No seed has been observed to date.

What is claimed is:

1. A new and distinct variety of *Lavandula* plant named 'VIOLET LACE' as described and illustrated herein.

* * * * *